United States Patent
Moszner et al.

(10) Patent No.: US 9,783,559 B2
(45) Date of Patent: Oct. 10, 2017

(54) β-KETOPHOSPHONIC ACIDS AND DENTAL MATERIALS BASED THEREON

(71) Applicant: Ivoclar Vivadent AG, Schaan (LI)

(72) Inventors: Norbert Moszner, Mauren (LI); Yohann Catel, Sargans (CH); Thorsten Bock, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 2 days.

(21) Appl. No.: 14/898,665

(22) PCT Filed: May 27, 2014

(86) PCT No.: PCT/EP2014/001421
§ 371 (c)(1),
(2) Date: Dec. 15, 2015

(87) PCT Pub. No.: WO2014/202176
PCT Pub. Date: Dec. 24, 2014

(65) Prior Publication Data
US 2016/0145277 A1    May 26, 2016

(30) Foreign Application Priority Data
Jun. 20, 2013  (EP) .................................... 13003143

(51) Int. Cl.
| A61K 6/08 | (2006.01) |
| A61K 6/00 | (2006.01) |
| C07F 9/38 | (2006.01) |
| C08F 230/02 | (2006.01) |
| A61K 6/083 | (2006.01) |
| C08F 222/38 | (2006.01) |

(52) U.S. Cl.
CPC ............ *C07F 9/3826* (2013.01); *A61K 6/083* (2013.01); *C07F 9/3808* (2013.01); *C08F 222/38* (2013.01); *C08F 230/02* (2013.01)

(58) Field of Classification Search
CPC ....... C08F 230/02; A61K 6/082; A61K 6/083; A61K 6/033
See application file for complete search history.

(56) References Cited

U.S. PATENT DOCUMENTS

| 6,160,015 | A | 12/2000 | Ratner | |
| 6,512,068 | B1 | 1/2003 | Nakatsuka | |
| 6,902,608 | B2 | 6/2005 | Erdmann et al. | |
| 7,183,038 | B2 * | 2/2007 | Yamasaki | B41C 1/1008 101/456 |
| 8,129,444 | B2 | 3/2012 | Hecht et al. | |
| 2005/0048398 | A1 | 3/2005 | Yamasaki et al. | |

FOREIGN PATENT DOCUMENTS

| CA | 2344134 A1 | 10/2001 | |
| CH | WO 2004026315 A1 * | 4/2004 | ............ C07F 9/4006 |
| DE | 19918974 A1 | 12/1999 | |
| DE | 10234326 B3 | 2/2004 | |
| EP | 1057468 A1 | 12/2000 | |
| EP | 2123246 A1 | 11/2009 | |

OTHER PUBLICATIONS

Bhattacharya, G., The Michaelis-Arbuzov Rearrangement, Chem. Rev. 81 (1981) 415-430.
Maloney, K.M., A General Procedure for the Preparation of B-Ketophosphonates, J. Org. Chem. 74 (2009) 7554-7576.
Koprowski, M., et al, Synthesis of B-Ketophosphonates with Electron Rich B-Aryl Groups as Useful Organophosphorus Reagents in Lignans Synthesis, Tetrahedron 65 (2009) 4017-4024.
Wei, W., et al., Catalytic and Direct Oxphosphorylation of Alkenes with Dioxygen and H-Phosphonates Leading to B-Ketophosphonates, Angew. Chem. 123 (2011) 9263-9265.
No, Joo Hwan, et al., Lipophilic Analogs of Zoledronate and Risedronate Inhibit Plasmodium Geranylgeranyl Diphosphate Synthase (GGPPS) and Exhibit Potent Antimalarial Activity, Proceedings of the national Academy of Sciences of the USA, Bd. 109; No. 11, 2012; pp. 4058-4063.
Norman, D., et al., Autotaxin Inhibition: Development and Application of Computational Tools to Identify Site-Selective Lead Compounds, Bioorganic & Medicinal Chemistry, Bd. 21, No. 17, 2013, pp. 5548-5560.
Norman, D., et al., Supporting Information, Autotaxin inhibition, Development and applicaton of computational tools to identify site-selective lead compounds; Bioorganic & Medicinal Chemistry, pp. S1-S21.
International Preliminary Report on Patentability of PCT/EP2014/001421, Dec. 22, 2015, 9 pages.
No, Joo Hwan et al., "Lipophilic analogs of zoledronate and risedronate inhibit Plasmodium geranylgeranyl diphosphate synthase (GGPPS) and exhibit potent antimalarial activity," Proceedings of the National Academy of Sciences of the United States of America, vol. 109, No. 11, 2012, pp. 4058-4063, XP002713050, ISSN: 0027-8424.

(Continued)

*Primary Examiner* — Sanza McClendon
(74) *Attorney, Agent, or Firm* — Ann M. Knab; Thad McMurray

(57) ABSTRACT

β-Ketophosphonic acid according to general formula I:

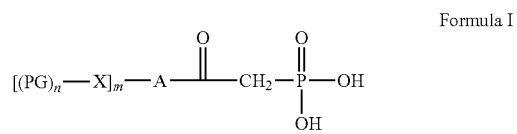

Formula I in which A=an aliphatic $C_1$-$C_{18}$ radical which can be interrupted by —O—, —S—, —CO—O— or —O—CO—C—; n=1, 2, 3 or 4; m=1 or 2; X=absent or a $C_1$-$C_{10}$ radical which can be interrupted by —O—, —S—, —CO—C—, —O—CO—NH— or —CO—NR$^1$—, wherein R$^1$ is H or $C_1$-$C_7$-alkyl; and PG=a group which can undergo free radical polymerization. The β-ketophosphonic acids are suitable in particular for the preparation of dental materials.

16 Claims, No Drawings

(56) References Cited

OTHER PUBLICATIONS

Norman, Derek D. et al., "Autotaxin Inhibition: Development and application of computational tools to identify site-selective lead compounds," Bioorganic & Medicinal Chemistry, vol. 21, No. 17, 2013, pp. 5548-5560, XP002713051, ISSN: 0968-0896.

Norman, Derek D. et al., "Autotaxin Inhibition: Development and application of computational tools to identify site-selective lead compounds," Bioorganic & Medicinal Chemistry, pp. S1-S21, XP002713891.

Kosobokov, M.D., "An Expedient Synthesis of Diethyl Diazomethylphosphonate", Mendeleev Communications 2011, 21, 142-143.

Fu, Y., et al., "Efficient Synthesis of Unsaturated 1-Monoacyl Glycerols for in meso Crystallization of Membrane Proteins," Synlett 2011, 6, 809-812, Georg Thieme Verlag Stuttgart, New York.

* cited by examiner

β-KETOPHOSPHONIC ACIDS AND DENTAL MATERIALS BASED THEREON

CROSS-REFERENCE TO RELATED APPLICATIONS

This application is a National Stage application of International Patent Application No. PCT/EP2014/001421 filed on May 27, 2014, which claims priority to European Patent Application No. 13003143.8 filed on Jun. 20, 2013, the disclosures of which are incorporated herein by reference in their entirety.

The invention relates to β-ketophosphonic acids which can undergo free radical polymerization and to dental materials which comprise such β-ketophosphonic acids. These dental materials are particularly suitable as adhesives, cements or coating materials.

Monomers which can undergo free radical polymerization and have acid groups are regularly employed for the preparation of dental materials. They impart to dental materials on the one hand self-etching properties, so that a treatment of the tooth surface with acid before application of the materials to etch the tooth surface and to remove the so-called smear layer can be dispensed with. They moreover improve the adhesion on the tooth by ionic or covalent interactions with the tooth substance.

The etching power of the monomers is largely determined by their acidity. This decreases from sulphonic acids via acid phosphates and phosphonic acids to carboxylic acids. Acid phosphates are currently chiefly used for the preparation of self-etching dental adhesives. Although sulphonic acids have a relatively high acidity, in practice only 2-acrylamido-2-methylpropanesulphonic acid is of relatively great importance, since the other properties of sulphonic acids, such as e.g. their polymerization ability and their ability to bond to the natural tooth substance, are not optimum.

EP 1 057 468 A1 discloses dental adhesives which comprise as the acid component monomers containing phosphate groups, such as methacryloyloxydecyl dihydrogen phosphate (MDP), methacryloyloxyethyl phenyl hydrogen phosphate (MEPP) or methacryloyloxyethyl dihydrogen phosphate (MEP). These monomers are still widely employed for the preparation of self-etching dental materials.

A disadvantage of these compounds is that they are not stable in aqueous solutions. Both their phosphoric acid ester bonds and their methacrylate ester bonds undergo hydrolytic cleavage in the presence of water. The hydrolysis is accelerated by the protons liberated by the acid monomers. Water is regularly employed as a solvent in self-etching dental materials, since it is necessary for the ionic processes which take place during etching of the tooth substance.

To improve the resistance of self-etching dental materials to hydrolysis, acid monomers have been proposed which have bonds between the polymerizable group and the acid group which are more stable to hydrolysis.

DE 100 18 968 C1 discloses polymerizable acrylphosphonic acids having a high stability to hydrolysis. In phosphonic acids the phosphoric acid ester bond is replaced by a direct bond between the carbon and phosphorus which is less susceptible to hydrolysis. The acrylphosphonic acids are further characterized in that the polymerizable group is preferably bonded via ether instead of ester functions.

DE 102 34 326 B3 relates to acrylic ester phosphonic acids, such as, for example, 2,4,6-trimethylphenyi-2-[4-(dihydroxyphosphoryl)-2-oxabutyl]acrylate, which has a particularly high stability to hydrolysis. The improved stability to hydrolysis is to be attributed to steric interactions.

DE 199 18 974 A1 discloses (meth)acrylates of hydroxyalkylphosphonates, such as 2-methacryloxyethanephosphonic acid (MAPA), which are said to be characterized by a strong and durable bonding to the tooth substrate. The stability of these monomers to hydrolysis, however, is not satisfactory.

EP 1 169 996 A1 relates to dental materials which are said to have good adhesion properties and a high stability to hydrolysis. The materials comprise polymerizable phosphonic acids, such as, for example, 1-(2,5-dimethyl-1,5-hexadienyl)-phosphonic acid (DMHD) and 4-methacrylamido-4-methylpentylphosphonic acid (MAMPA). DHMD at least is not very suitable for free radical polymerization.

A disadvantage of phosphonic acids compared with the acid phosphates is their lower acidity and the associated lower etching power with respect to tooth enamel and dentine.

The object of the invention is to provide acid polymerizable monomers which are suitable in particular for the preparation of dental materials and which have a high stability to hydrolysis in combination with a high acidity. Furthermore, the monomers are to have a profile of properties which is required for dental uses. In particular, they are to be readily soluble in polar solvents and in mixtures of polar solvents and water, have a high polymerization rate in free radical polymerization and show a good adhesion to the tooth structure and in particular to tooth enamel.

The object is achieved according to the invention by β-ketophosphonic acids according to general formula I:

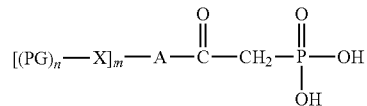

Formula I in which
A=an aliphatic $C_1$-$C_{18}$ radical which can be interrupted by —O—, —S—, —CO—O—, or —O—CO—O—,
n=1, 2, 3 or
m=1 or 2,
X=absent or a $C_1$-$C_{10}$ radical which can be interrupted by —O—, —S—, —CO—O—, —O—CO—NH— or —CO—NR$^1$—, wherein R$^1$ is H or $C_1$-$C_5$-alkyl, preferably H, $CH_3$ or $C_2H_5$, and
PG=a group which can undergo free radical polymerization.

The group A is an aliphatic group which is substituted m times by the radical [(PG)$_n$-X] or n times by PG, if X is absent, and once by the β-ketophosphonic acid group. The formula includes only those compounds which are compatible with chemical valence theory. Thus, if A for example comprises only one carbon atom, this carbon atom can carry a maximum of four substituents.

The indication that a radical is interrupted by hetero atoms or functional groups is to be understood as meaning that the hetero atoms or functional groups are inserted into the carbon chain and are delimited on both sides by C atoms. A line of hetero atoms and/or functional groups does not fail under this definition.

Preferably, A is not interrupted or is interrupted by 1 to 4, in particular 1 to 2 hetero atoms or functional groups, particularly preferably by 1 or 2 O atoms.

X is an aliphatic group which is substituted n times by PG and which is bonded to A via a further bond. X is preferably a $C_1$-$C_{10}$-alkylene group, in particular a linear alkylene group. X can be interrupted by —O—, —S—, —CO—O—, —O—CO—NH— or —CO—NR$^1$—, wherein X is preferably not interrupted by hetero atoms or functional groups.

PG is a group which can undergo free radical polymerization. Preferred groups which can undergo free radical polymerization are vinyl, allyl, CH$_2$=CR$^2$—CO—Y—, R$^3$O—CO—(=CH$_2$)—CH$_2$—Y—, wherein Y is O or NR$^4$ or is absent, R$^2$ is H or CH$_3$ and R$^3$ and R$^4$ independently of each other are each H or a C$_1$-C$_7$-alkyl. (Meth)acryloyloxy groups (CH$_2$=CR$^2$—CO—Y— where Y=O) are particularly preferred, in particular (meth)acryloylamino groups (CH$_2$=CR$^2$—CO—Y— where Y=NR$^4$) and R$^3$O—CO—C(=CH$_2$)—CH$_2$—Y— (where Y=preferably O); R$^2$ is in each case H or CH$_3$, R$^3$ is CH$_3$ or C$_2$H$_5$ and R$^4$ is H, CH$_3$ or C$_2$H$_5$.

The abovementioned preferred definitions of the variables can be chosen independently of each other. According to the invention, however, those compounds in which all the variables have one of the preferred and in particular one of the particularly preferred definitions are naturally particularly preferred.

Compounds in which the variables are defined as follows are thus preferred:

A=an aliphatic C$_2$-C$_{15}$ radical which can be interrupted by —O—, preferably a linear C$_5$-C$_{10}$ radical which can be interrupted by 1 or 2 O atoms, n=1 or 2, preferably 1, m=1 or 2, X=a C$_1$-C$_4$-alkylene radical or is absent, preferably a C$_1$ or C$_2$ radical or is absent, and PG=vinyl, ally, CH$_2$=CR$^2$—CO—Y— or R$^3$O—CO—C(=CH$_2$)—CH$_2$—Y—, wherein Y is O or NR$^4$ or is absent, R$^2$ is H or CH$_3$ and R$^3$ and R$^4$ independently of each other are each H or a C$_1$-C$_7$-alkyl; particularly preferably CH$_2$=CR$^2$—CO—Y—, where Y=O or NR$^4$, or R$^3$O—CO—C(=CH$_2$)—CH$_2$Y—, where Y=O; R$^2$=H or CH$_3$, R$^3$=CH$_3$ or C$_2$H$_5$ and R$^4$=H, CH$_3$ or C$_2$H$_5$.

The polymerizable β-ketophosphonic acids of general formula I can be easily prepared. For example, OH-functionalized β-ketophosphonates can be reacted with COOH-alkyl-functionalized polymerizable radicals to give the corresponding polymerizable β-ketophosphonates and then by silylation with e.g. trimethyisilyi bromide (TMSiBr) and methanolysis to give the polymerizable β-ketophosphonic acids of general formula I:

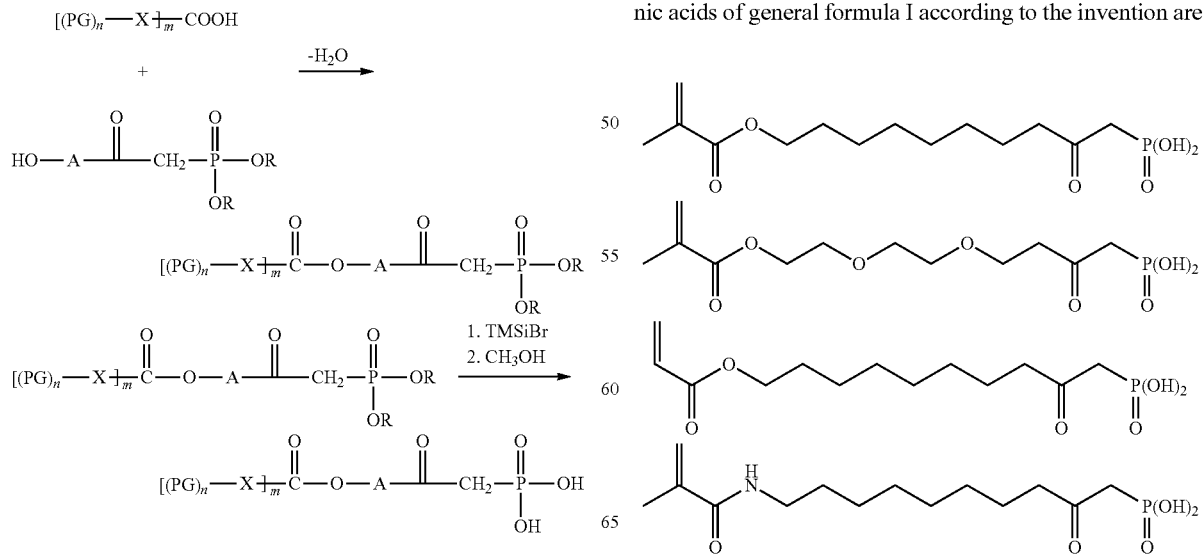

Specifically e.g. methacrylic acid 3-carboxypropyl ester can be reacted with 5-hydroxy-2-oxopentylphosphonic acid diethyl ester with subsequent liberation of the phosphonic acid groups:

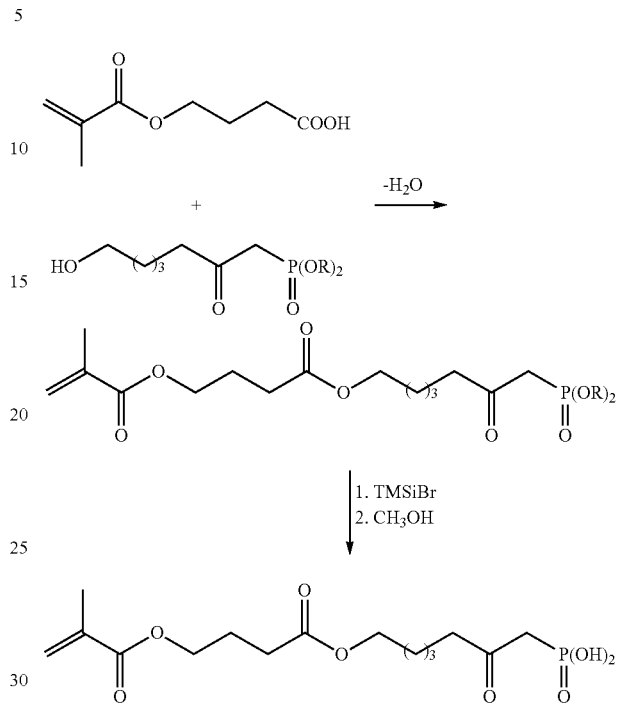

In this context ketophosphonates can be prepared according to the Arbuzov reaction by reaction of α-haloketones with trialkyl phosphites (cf. e.g. A. K. Bhattacharya, G. Thyagarajan, Chem. Rev. 81 (1981) 415-430), by acylation of alkylphosphonates with carboxylic acid derivatives in the presence of a stoichiometric amount of organometallic reagent (cf. e.g. K. M. Maloney, J. Y. L. Chung, J. Org. Chem. 74 (2009) 7554-7576), by oxidation of β-hydroxyalkylphosphonates (cf. e.g. Koprowski et al., Tetrahedron 65 (2009) 4017-4024) and by direct or catalytic oxyphosphorylation of alkenes with O$_2$ and H-phosphonates (K. Wie, J.-X. Ji, Angew. Chem. 123 (2011) 9263-9265).

Preferred examples of the polymerizable β-ketophosphonic acids of general formula I according to the invention are:

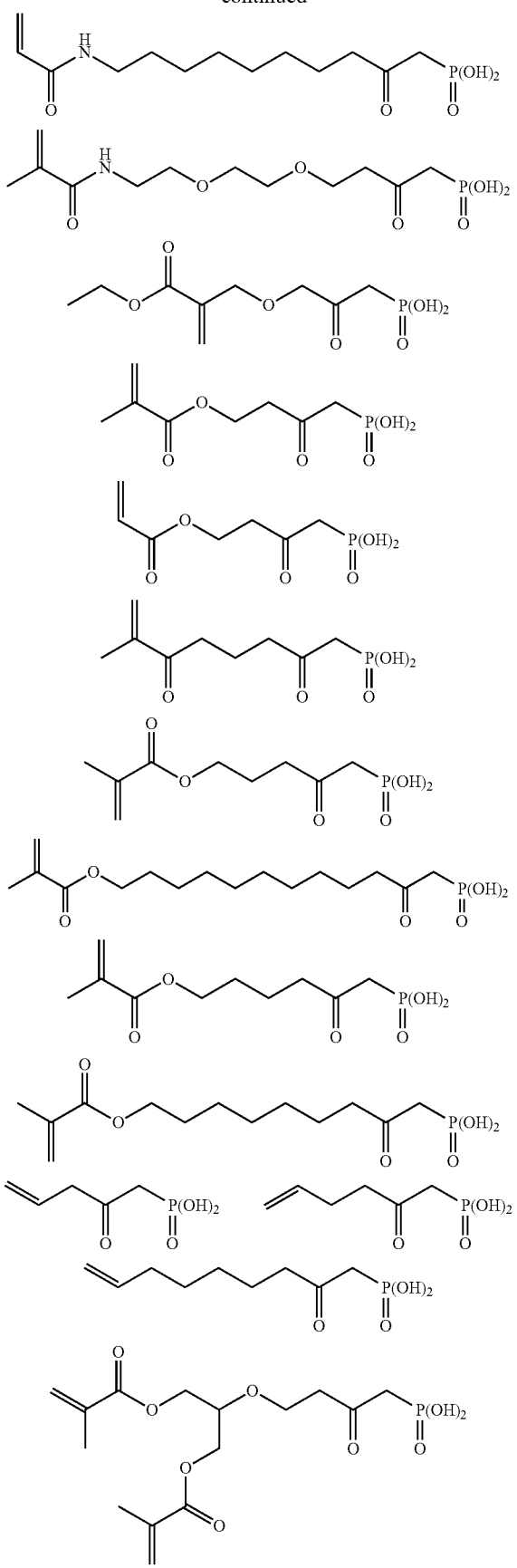

The polymerizable β-ketophosphonic acids of general formula I are suitable in particular for the preparation of dental materials, in particular of dental materials having self-etching properties. They are very readily soluble in alcohols, such as e.g. ethanol and isopropanol, and in acetone or in aqueous mixtures thereof. Compared with known polymerizable alkyl phosphonic acids having a comparable spacer length, for example the aqueous-alcoholic solutions surprisingly show a significantly lower pH, i.e. they are significantly more acid, which is advantageous with respect to the self-etching properties. They moreover show a high adhesion to enamel compared with conventional alkylphosphonic acids. A further advantage is their improved stability to hydrolysis compared with acid phosphates. The β-ketophosphonic acids according to the invention therefore combine the high stability to hydrolysis of phosphonic acids with the high acidity of phosphoric acid esters.

The β-ketophosphonic acids of Formula I are preferably employed in an amount of from 0.1 to 50 wt.-%, particularly preferably 1 to 40 wt.-% and very particularly preferably in an amount of from 2 to 30 wt.-%, based on the total weight of the dental material.

The dental materials according to the invention based on the polymerizable β-ketophosphonic acids of general formula I can preferably comprise further monomers (comonomers) which can undergo free radical polymerization, particularly preferably mono- or polyfunctional (meth)acrylic acid derivatives. Monofunctional monomers are understood as meaning monomers having one, and polyfunctional monomers are understood as meaning monomers having two or more, preferably two to four groups which can undergo free radical polymerization. Examples in this respect are methyl, ethyl, hydroxyethyl, butyl, benzyl, tetrahydrofurfuryl or isobornyl(meth)acrylate, bisphenol A di(meth)acrylate, Bis-GMA (an addition product of methacrylic acid and bisphenol A digiycidyl ether), UDMA (an addition product of 2-hydroxyethyl methacrylate (HEMA) and 2,2,4-trimethylhexamethylene-diisocyanate), di-, tri- or tetraethylene glycol di(meth)acrylate, trimethylolpropane tri(meth)acrylate, pentaerythritol tetra(meth)acrylate and glycerol di(meth) acrylate, 1,4-butanediol di(meth)acrylate, 1,10-decanediol di(meth)acrylate or 1,12-dodecanediol di(meth)acrylate.

Further preferred comonomers are N-mono- or -disubstituted acrylamides, such as e.g. N-ethylacrylamide, N,N-dimethylacrylamide, N-(2-hydroxyethyl)acrylamide or N-methyl-N-(2-hydroxyethyl)acrylamide, or N-monosubstituted meth-acrylamides, such as e.g. N-ethylmethacrylamide or N-(2-hydroxyethyl)methacrylamide, and N-vinylpyrrolidone or allyl ether. These monomers are characterized by a high stability to hydrolysis and a relatively low viscosity and are therefore suitable, for example, as diluting monomers.

Comonomers which are likewise preferred are crosslinking pyrrolidones, such as e.g. 1,6-bis(3-vinyl-2-pyrrolidonyl) hexane, or commercially available bisacrylamides, such as methylene- or ethylenebisacrylamide, or bis(meth)acrylamides, such as e.g. N,N'-diethyl-1,3-bis(acrylamido)propane, 1,3-bis(methacrylamido)propane, 1,4-bis(acrylamido) butane or 1,4-bis(acryloyl)piperazine, which can be synthesized by reaction of the corresponding diamines with (meth)acrylic acid chloride. These monomers are also characterized by a high stability to hydrolysis. They contain two or more groups which can undergo free radical polymerization and are therefore suitable e.g. as crosslinking monomers.

A mixture of monofunctional and crosslinking monomers is preferably used as comonomers, wherein monomer mixtures which comprise 2-hydroxyethyl methacrylate in combination with Bis-GMA, UDMA, triethylene glycol dimethacrylate and/or decanediol dimethacrylate are particularly advantageous.

Finally mixtures of one or more of the abovementioned monomers with further adhesive monomers which contain acid groups and can undergo free radical polymerization can also be used. Suitable monomers containing acid groups are polymerizable carboxylic acids, such as maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxy-propyl)-N-phenylglycine or 4-vinylbenzoic acid. Examples of suitable phosphonic acid monomers are vinylphosphonic acid, 4-vinylphenylphosphonic acid, 4-vinylbenzylphosphonic acid, 2-methacryloyloxyethylphosphonic acid, 2-methacrylamido-ethylphosphonic acid, 4-methacrylamido-4-methylpentylphosphonic acid, 2-[4-(dihydroxyphosphoryl)-2-oxabutyl]acrylic acid or 2-[4-(dihydroxyphosphoryl)-2-oxabutyl]acrylic acid ethyl or 2,4,6-trimethylphenyl ester. Examples of suitable acid polymerizable phosphoric acid esters are 2-methacryloyloxypropyl mono- or dihydrogen phosphate, 2-methacryloyloxyethyl mono- or dihydrogen phosphate 2-methacryloyloxyethyl phenyl hydrogen phosphate, dipentaerythritol pentamethacryloyloxyphosphate, 10-methacryloyloxydecyl dihydrogen phosphate, phosphoric acid mono-(1-acryloylpiperidin-4-yl) ester, 6-(methacrylamido)hexyl dihydrogen phosphate and 1,3-bis(N-acryloyl-N-propylamino)propan-2-yl dihydrogen phosphate. Examples of suitable polymerizable sulphonic acids are vinylsulphonic acid, 4-vinylphenylsulphonic acid or 2-(methacrylamido)propylsulphonic acid. The total amount of further monomers containing acid groups is preferably chosen such that it does not exceed the amount of ketophosphonic acid (s) of Formula I and particularly preferably is below this.

For initiation of the free radical polymerization, the dental materials according to the invention preferably comprise an initiator for the free radical polymerization. For the photopolymerization, benzophenone, benzoin and derivatives thereof or α-diketones or derivatives thereof, such as 9,10-phenanthrenequinone, 1-phenylpropane-1,2-dione, diacetyl or 4,4'-dichlorobenzil, are preferably employed. Preferably, camphorquinone and 2,2-dimethoxy-2-phenylacetophenone and particularly preferably α-diketones in combination with amines as reducing agents, such as e.g. 4-(dimethylamino) benzoic acid esters, N,N-dimethylaminoethyl methacrylate, N,N-dimethyl-sym.-xylidine or triethanolamine, are used. Norrish type I photoinitiators are also particularly suitable, above all acyl- or bisacylphosphine oxides, monoacyltrialkyl- or diacyldialkylgermanium compounds, such as e.g. benzoyltrimethylgermanium, dibenzoyldiethylgermanium or bis(4-methoxybenzoyl)diethylgermanium. Mixtures of the various photoinitiators, such as e.g. dibenzoyldiethylgermanium in combination with camphorquinone and 4-dimethylaminobenzoic acid ethyl ester, can also be employed.

Initiators which are used for a polymerization carried out at room temperature are redox initiator combinations, such as e.g. combinations of benzoyl peroxide with N,N-dimethyl-sym.-xylidine, N,N-dimethyl-p-toludine, N,N-diethyl-3,5-di-tert-butylaniline or N,N-diethanol-p-toluidine. Redox systems comprising peroxides or hydroperoxides and reducing agents, such as e.g. ascorbic acid, barbiturates, thioureas or sulphinic acids, are moreover also particularly suitable.

The dental materials according to the invention preferably comprise a photoinitiator or a combination of a photoinitiator and a redox initiator, preferably a peroxide. A particularly advantageous initiator combination for the dual curing is a mixture of camphorquinone and benzoyl peroxide, wherein these initiators are also preferably combined with an amine.

The compositions employed according to the invention furthermore preferably comprise organic or inorganic filler particles for improving the mechanical properties or for adjusting the viscosity. Fillers for adapting the mechanical properties preferably have an average particle diameter of from 10 nm to 10 μm, preferably from 10 nm to 1.0 μm, and fillers for adjusting the viscosity preferably from 10 to 1,000 nm, preferably from 10 to 200 nm. These filler types are preferably employed together. Unless stated otherwise, the average particle diameter is the weight-average value.

Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate or microfine fillers, such as pyrogenic silica or precipitated silica, and mini-fillers, such as quartz, glass ceramic or glass powder having an average particle diameter of from 0.01 to 1 μm, and radiopaque fillers, such as ytterbium trifluoride or nanoparticulate tantalum(V) oxide or barium sulphate. Preferred organic fillers are fillers based on poly(meth)acrylates, such as e.g. PMMA, or cellulose derivatives, such as e.g. carboxymethylcellulose, which are ground to the abovementioned particle size after curing. The organic fillers can in turn have a filler content of the inorganic fillers mentioned.

Solvent-containing dental materials represent a further preferred embodiment of the invention. In particular water and polar organic solvents, such as acetone, isopropanol and, in particular, ethanol and mixtures of these solvents come into consideration here. Mixtures of water and polar organic solvents, in particular mixtures of water and ethanol, water and acetone or water, ethanol and acetone, are particularly preferred.

The compositions employed according to the invention can optionally comprise further additives, such as e.g. stabilizers, flavour substances, colorants, microbicidal active compounds, additives which release fluoride ions, optical brighteners, plasticizers and/or UV absorbers.

Dental materials according to the invention which comprise the following components are preferred:

a) 0.1 to 50 wt.-%, preferably 1 to 40 wt.-% and particularly preferably 2 to 30 wt.-% of polymerizable β-ketophosphonic acids of general formula I,
b) 0.01 to 10 wt.-%, particularly preferably 0.1 to 3.0 wt.-% of initiator,
c) 0 to $0 wt.-%, preferably 0 to 60 wt.-% and particularly preferably 5 to 50 wt.-% of additional monomers,
d) 0 to $0 wt.-% of filler,
e) 0 to 70 wt.-%, preferably 0 to 60 wt.-% and particularly preferably 0 to 50 wt.-% of solvent, and optionally
f) 0.01 to 10 wt.-%, preferably 0.01 to 3 wt.-% of further additives.

The dental materials according to the invention preferably comprise as additional monomers (c) 5 to 40 wt.-% of non-acid mono- or multifunctional monomers and/or 0 to 60 wt.-%, preferably 0 to 30 wt.-% of acid monomers.

The amount of filler or fillers (d) depends on the intended use. Dental materials for use as adhesives preferably comprise 0 to 20 wt.-% and dental materials for use as cement or filling material (composite) preferably comprise 20 to 80 wt.-% of filler. Dental materials for use as cement or filling material preferably comprise no solvent.

Dental materials for use as adhesives preferably have the following composition:

a) 0.1 to 50 wt.-%, preferably 1 to 40 wt.-% and particularly preferably 2 to 30 wt.-% of polymerizable β-ketophosphonic acids of general formula I,
b) 0.01 to 10 wt.-%, particularly preferably 0.1 to 3.0 wt.-% of initiator,
c) 0 to 60 wt.-%, preferably 0 to 40 wt.-% and particularly preferably 5 to 40 wt.-% of non-acid mono- or multifunctional monomers and/or 0 to 60 wt.-% and preferably 0 to 30 wt.-% of acid comonomers,
d) 0 to 20 wt.-% of fillers,
e) 0 to 70 wt.-%, preferably 0 to 60 wt.-% and particularly preferably 0 to 50 wt.-% of solvent, preferably water or a mixture of water, ethanol and/or acetone, and optionally
f) 0.01 to 3 wt.-% of further additives.

All the percentages relate in each case to the total weight of the composition.

Those dental materials which consist of the components mentioned are particularly preferred. Those materials in which the individual components are in each case chosen from the abovementioned preferred and particularly preferred substances are furthermore preferred.

The dental materials are particularly suitable as adhesives, cements, filling materials or coating materials. The dental dentist for restoration of damaged teeth (clinical materials). However, they can also be employed extraorally, for example in the production or repair of dental restorations (technical grade materials).

The invention is explained in more detail below with the aid of examples.

EXAMPLES

Example 1

Synthesis of 9-methacryloyloxy-2-oxononylphosphonic Acid (MOPA)

a) Synthesis of 2-oxo-9-THP-oxynonylphosphonic Acid Diethyl Ester 1

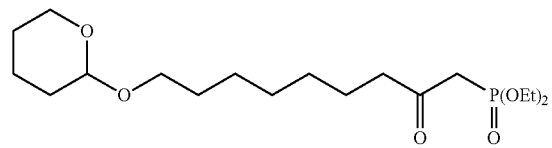

A solution of commercially available diethyl (2-oxopropyl)phosphonate (10.0 g, 51.5 mmol, 1.1 equivalents), which was prepared analogously to the literature (Kosobokov, M. P. Titanyuk, I. D.; Reletskaya, I. P. Mendeleev Communications 2011, 21, 142-143), in dry THF (15 ml) was added dropwise to a stirred mixture of NaH (2.27 g, 56.7 mmol, 1.2 equivalents), a 60% dispersion in mineral oil, which had been prewashed with hexane (2×20 ml), in dry THF (20 ml) at 0° C. The reaction mixture was heated to room temperature, stirred for 1 h and then cooled again to 0° C., a solution of n-BuLi (22.5 ml of a 2.5 M solution in hexane, 56.2 mmol, 1.2 equivalents) was added dropwise and the solution was stirred at 0° C. for 30 min. A solution of 2-(6-bromohexyloxy)tetrahydro-2H-pyran (12.4 g, 46.8=01), which was prepared analogously to the literature (Fu, Y.; Weng, Y. Wen-Xu, H. Qinghai, Z. Synlett 2011, 6, 809-812), in dry THF (15 ml) was then added and the reaction mixture was heated to room temperature and stirred for 15 h. The reaction product was then introduced carefully into ice-cooled aqueous $NH_4Cl$ solution (150 ml) and the aqueous phase was extracted with diethyl ether (3×100 ml). The combined organic phases were dried over anhydrous $Na_2SO_4$ and concentrated in vacuo. The crude product obtained was purified by flash column chromatography (eluent: ethyl acetate/hexane: 75/25) and gave 9.6 g (25.4 mmol) of the phosphonate 1 as a pale yellowish liquid. Yield: 54%.

$^1$H NMR (400 MHz, $CDCl_3$): δ=1.23-1.40 (in, 6H, $CH_2$); 1.35 (t, $^3J_{HH}$=7.0 Hz, 6H, $POCH_2\underline{CH}_3$); 1.46-1.63 (m, 8H, $CH_2$); 1.65-1.76 (m, 1H, $CH_2$); 1.77-1.89 (m, 1H, $CH_2$); 2.61 (t, $^3J_{HH}$=7.3 Hz, 2H, $\underline{CH}_2CH_2C$=O); 3.07 (d, $^2J_{HP}$=22.8 Hz, 2H, $CH_2P$); 3.37 (dt, $^2J_{HH}$=9.6 Hz, $^3J_{HH}$=6.5 Hz, 1H, $CH_2O$); 3.46-3.54 (m, 1H, $CH_2O$); 3.72 (dt, $^2J_{HE}$=9.6 Hz, $^3J_{HH}$=6.9 Hz, 1H, $CH_2O$); 3.83-3.90 (m, 1H, $CH_2O$); 4.09-4.20 (m, 4H, $PO\underline{CH}_2CH_3$); 4.54-4.59 (m, 1H, $O\underline{CH}O$).

$^{31}$P NMR (162 MHz, $CDCl_3$): 20.0.

$^{13}$C NMR (101 MHz, $CDCl_3$): δ=16.3 (d, $^3J_{CF}$=6.3 Hz, $POCH_2\underline{CH}_3$); 19.7 ($CH_2$); 23.3 ($CH_2$); 25.5 ($CH_2$); 26.0 ($CH_2$); 28.9 ($CH_2$); 29.2 ($CH_2$); 29.7 ($CH_2$); 30.8 ($CH_2$); 42.4 (d, $^1J_{CP}$=127.3 Hz, $CH_2P$); 44.0 ($\underline{CH}_2CH_2C$=O); 62.3 ($CH_2O$); 62.4 (d, $^2J_{CP}$=6.4 Hz, $PO\underline{CH}_2CH_3$) 67.5 ($CH_2O$); 98.8 ($O\underline{CH}O$); 202.1 (d, $^2J_{CP}$=6.0 Hz, C=O).

b) 9-Hydroxy-2-oxononylphosphonic Acid Diethyl Ester 2

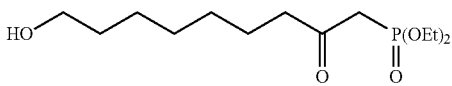

The phosphonate 1 (47.2 mmol) and pyridinium toluenesulphonate (1.19 g, 4.72 mmol) were added to ethanol (500 ml) and the mixture was stirred at 55° C. for 3 h and then concentrated in vacuo. The crude product obtained was purified by flash column chromatography (eluent: ethyl acetate/hexane: 95/5) and gave 11.04 g (37.6 mmol) of the phosphonate 2 as a pale yellowish liquid. Yield: 80%.

$^1$H NMR (400 MHz, CDCl$_3$): δ=1.26-1.40 (m, 6H, CH$_2$); 1.34 (t, $^3J_{HH}$=6.9 Hz, 6H, POC$\underline{H_2}$CH$_3$); 1.51-1.64 (m, 4H, CH$_2$); 2.62 (t, $^3J_{HH}$=7.4 Hz, 2H, CH$_2$C$\underline{H_2}$C=O); 3.07 (d, =22.8 Hz, 2H, CH$_2$P); 3.63 (t, $^3J_{HH}$=6.6 Hz, 2H, CH$_2$OH); 4.09-4.20 (m, 4H, POC$\underline{H_2}$CH$_3$).

$^{31}$P NMR (102 MHz, CDCl$_3$): 20.0.

$^{13}$C NMR (101 MHz, CDCl$_3$): δ=16.2 (d, $^3J_{CP}$=6.2 Hz, POCH$_2\underline{C}$H$_3$); 23.2 (CH$_2$); 25.5 (CH$_2$); 28.8 (CH$_2$); 29.0 (CH$_2$); 32.7 (CH$_2$); 42.3 (d, $^1J_{CP}$=127.3 Hz, CH$_2$P); 43.9 (CH$_2\underline{C}$H$_2$C=O); 62.5 (d, $^2J_{CP}$=6.5 Hz, POC$\underline{C}$H$_2$CH$_3$); 62.7 (CH$_2$OH); 202.1 (d, $^2J_{CP}$=6.2 Hz, C=O).

c) 9-Methacryloyloxy 2-oxononylphosphonic Acid Diethyl Ester 3

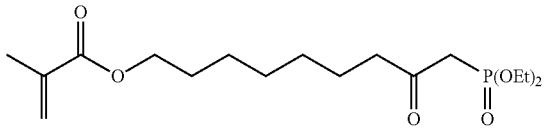

Methacrylic anhydride (6.14 ml, 41.2 mmol, 1.1 equivalents) was added dropwise, with stirring, to a solution of the hydroxyphosphonate 2 (37.5 mmol), triethylamine (5.75 ml, 41.2 mmol, 1.1 equivalents) and 4-dimethylaminopyridine (229 mg, 1.9 mmol, 5 mol.-%) in anhydrous methylene chloride (100 ml). After stirring for 15 h, the reaction mixture was washed with distilled water (100 ml) and the organic phase was separated off, dried over anhydrous Na$_2$SO$_4$ and concentrated in vacuo. The crude product obtained was purified by flash column chromatography (eluent: ethyl acetate/hexane: 80/20) and gave 11.53 q (31.9 mmol) of the phosphonate 3 as a pale yellowish liquid. Yield: 85%.

$^1$H NMR (400 MHz, CDCl$_3$): δ=1.23-1.42 (m, 6H, CH$_2$); 1.32 (t, $^3J_{HH}$=7.1 Hz, 6H, POCH$_2\underline{C}$H$_3$); 1.52-1.70 (m, 4H, CH$_2$); 1.93 (1s, 3H, CH$_3$); 2.61 (t, $^3J_{HH}$=7.3 Hz, 2H, CH$_2$C$\underline{H_2}$C=O); 3.05 (d, 22.9 Hz, 2H, CH$_2$P) 4.08-4.19 (m, 6H, POC$\underline{H_2}$CH$_3$ and CH$_2$OC=O); 5.51-5.55 (m, 1H, CH$_2$=C); 6.08 (1s, 1H, CH$_2$=C).

$^{31}$P NMR (162 MHz, CDCl$_3$): 20.0.

$^{13}$C NMR (101 MHz, CDCl$_3$) δ=16.3 (d, $^3J_{CP}$=6.3 Hz, POCH$_2\underline{C}$H$_3$); 18.3 (CH$_3$); 23.3 (CH$_2$); 25.8 (CH$_2$); 28.5 (CH$_2$); 28.8 (CH$_2$); 29.0 (CH$_2$); 42.4 (d, $^1J_{CP}$=127.13 Hz, CH$_2$P); 44.0 (CH$_2\underline{C}$H$_2$C=O); 62.5 (d, $^2J_{CP}$=6.4 Hz, POC$\underline{C}$H$_2$CH$_3$); 64.7 ($\underline{C}$H$_2$OC=O); 125.1 ($\underline{C}$H$_2$=C); 136.5 (CH$_2$=$\underline{C}$); 167.5 (OC=O); 202.0 (d, $^2J_{CP}$=6.2 Hz, PCH$_2$C=O).

d) 9-Methacryloyloxy-2-oxononylphosphonic Acid (MOPA)

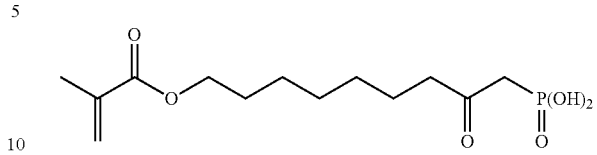

Trimethylsilyl bromide (12.5 ml, 94.7 mmol, 3.0 eq.) was added to a solution of the phosphonate 3 (11.43 g, 31.6 mmol) in anhydrous methylene chloride (100 ml) and the mixture was stirred at 30° C. for 5 h. Thereafter, the reaction product was concentrated in vacuo, methanol (100 ml) was added and the mixture was stirred at room temperature for 30 min. After addition of BHT (250 ppm) the solution was concentrated to constant weight under a fine vacuum and gave 9.6 g (31.4 mmol) of the ketophosphonic acid MOPA as a pale yellowish liquid. Yield: 99%.

$^1$H NMR (400 MHz, CDCl$_3$): δ=1.23-1.42 (m, 6H, CH$_2$); 1.52-1.71 (m, 4H, CH$_2$); 1.94 (1s, 3H, CH$_3$); 2.63 (t, $^3J_{HH}$=7.3 Hz, 2H, CH$_2\underline{C}$H$_2$C=O); 3.19 (d, $^2J_{HH}$=22.7 Hz, 2H, CH$_2$P); 4.13 (t, $^3J_{HH}$=6.6 Hz, 2H, CH$_2$OC=O); 5.54-5.58 (m, 1H, CH$_2$=C); 6.09 (1s, 1H, CH$_2$=C); 10.25 (1s, 2H, POH).

$^{31}$P NMR (162 MHz, CDCl$_3$): 22.2.

$^{13}$C NMR (101 MHz, CDCl$_3$): δ=18.3 (CH$_3$); 23.2 (CH$_2$); 25.7 (CH$_2$); 28.5 (CH$_2$); 28.7 (CH$_2$); 28.9 (CH$_2$); 42.3 (d, $^1J_{CF}$=131.3 Hz, CH$_2$P); 44.2 (CH$_2\underline{C}$H$_2$C=O); 64.9 (CH$_2$OC=O); 125.5 (CH$_2$=C); 136.4 (CH$_2$=$\underline{C}$); 167.8 (OC=O); 204.6 (d, $^2J_{CP}$=6.4 Hz, PCH$_2$C=O).

Example 2

Investigation of the Photopolymerization of 9-methacryloyloxy-2-oxononylphosphonic Acid MOPA by Means of DSC 0.1 wt.-% of the photoinitiator bis(4-methoxybenzoyl)-diethylgermanium was added to a mixture of the crosslinking agent N,N'-diethyl-1,3-bis(acrylamido)propane (DEPBA) and MOPA in the molar ratio of 8:2. The mixture was polymerized in a differential scanning calorimeter (Diamond, Perkin Elmer) with a photopolymerization attachment by irradiation with an LED lamp (Bluephase, Ivoclar Vivadent) for 2 minutes at 37° C. A similarly high maximum polymerization rate (0.078 s$^{-1}$) compared with the pure crosslinking agent and a coinciding double bond conversion (63%) of the mixture resulted.

Example 3

Determination of the pH of an MOPA Solution

The pH of 20% solutions of MOPA, 10-(methacryloyloxy)decyl dihydrogen phosphate (MDP) and 10-(methacryloyloxy)decylphosphonic acid (MDPA) in a mixture in the weight ratio of 1:1 of water and ethanol was determined. A pH of 1.9 resulted for MOPA, while for the dihydrogen phosphate MDP a pH of 1.6 and for the phosphonic acid monomer MDPA a pH of 2.3 was determined. It is thus found surprisingly that the ketophosphonic acid investigated is significantly more strongly acid than an alkylphosphonic acid having a similar C number of the spacer group.

Example 4

Adhesives and Adhesion Investigations Based on methacryloyloxy-2-oxononylphosphonic Acid MOPA To investigate the adhesion to dentine and enamel on bovine teeth, adhesives having the composition shown in Table 1 were prepared. Bovine teeth were embedded in a cylinder of plastic such that the dentine or the enamel and the plastic were in one plane. A layer of adhesive of the above composition was painted on with a microbrush, and the adhesive was agitated on the tooth structure for approx. 20 s, blown on briefly with an air fan to remove the solvent and exposed to light with an LED lamp (Bluephase, Ivoclar Vivadent) for 10 s. A cylinder of composite of Tetric® EvoCeram (Ivoclar Vivadent) was polymerized onto the layer of adhesive.

The test specimens are then stored in water at 37° C. for 24 h and the shear adhesive strength determined in accordance with the ISO guideline "ISO 2003-ISO TR 11405: Dental Materials Guidance on Testing of Adhesion to Tooth Structure": Adhesive A: dentine: 34.4 MPa and enamel 30.3 MPa; Adhesive B: 22.6 MPa and enamel 16.8 MPa.

The results demonstrate that enamel/dentine adhesives based on the polymerizable β-ketophosphonic acids give high enamel and dentine adhesion values with dental composites.

TABLE 1

Composition of the adhesives (data in % by weight)

| Component | Adhesive A | Adhesive B (comparison) |
|---|---|---|
| MOPA | 15.0 | — |
| MDPA | — | 15.0 |
| Bis-GMA[1) | 19.0 | 19.0 |
| DEPBA | 43.2 | 43.2 |
| Aerosil R709[2) | 1.4 | 1.4 |
| Photoinitiator[3) | 2.6 | 2.6 |
| Deionized water | 14.6 | 14.6 |
| Isopropanol | 4.2 | 4.2 |

[1)Addition product of methacrylic acid and bisphenol A diglycidyl ether
[2)Methacrylosilanized pyrogenic silica having an average particle size of 40 nm (Degussa)
[3)Mixture of camphorquinone (0.9%), 4-dimethylbenzoic acid ethyl ester (0.4%) and the acylphosphine oxide Lucerin TPO (BASF; 1.3%)

The invention claimed is:

1. Dental material comprising
at least one β-Ketophosphonic acid according to general formula I:

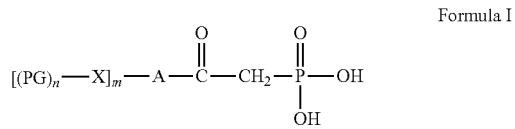

Formula I in which
A=an aliphatic $C_1$-$C_{18}$ radical which can be interrupted by —O—, —S—, —CO—O— or —O—CO—O—,
n=1, 2, 3 or 4,
m=1 or 2,
X=absent or a $C_1$-$C_{10}$ radical which can be interrupted by —O—, —S—, —CO—O—, —O—CO—NH— or —CO—NR$^1$—, wherein R$^1$ is H or $C_1$-$C_6$-alkyl, and
PG=a group which can undergo free radical polymerization; and
at least one initiator for free radical polymerization.

2. Dental material according to claim 1, wherein
A=an aliphatic $C_2$-$C_{15}$ radical which can be interrupted by —O—,
n=1 or 2,
m=1 or 2,
X=a $C_1$-$C_4$-alkylene radical or is absent, and
PG=vinyl, allyl, $CH_2$=$CR^2$—CO—Y— or $R^3$O—CO—C(=$CH_2$)—$CH_2$—Y—, wherein Y is O or $NR^4$ or is absent, $R^2$ is H or $CH_3$ and $R^3$ and $R^4$ independently of each other are each H or $C_1$-$C_7$-alkyl.

3. Dental material according to claim 2, wherein
A=a linear aliphatic $C_1$-$C_{10}$ radical which can be interrupted by 1 or 2 —O—,
n=1,
m=1 or 2,
X=a $C_1$-$C_2$ radical or is absent,
PG=$CH_2$=$CR^2$—CO—Y—, wherein Y is O or $NR^4$, or $R^3$O—CO—C(=$CH_2$)—$CH_2$—Y—, wherein Y is O, and wherein $R^2$ is H or $CH_3$, $R^3$ is $CH_3$ or $C_2H_5$ and $R^4$ is H, $CH_3$ or $C_2H_5$.

4. Dental material according to claim 1, which additionally comprises a further monomer which can undergo free radical polymerization.

5. Dental material according to claim 4, which comprises as further monomer one or more mono- and/or polyfunctional (meth)acrylic acid derivatives and/or (meth)acrylamide derivatives.

6. Dental material according to claim 1, which additionally comprises at least one solvent.

7. Dental material according to claim 6, which comprises as solvent water or a mixture of water and a polar organic solvent.

8. Dental material according to claim 1, which comprises
a) 0.1 to 50 wt.-% of β-ketophosphonic acid of general formula I,
b) 0.01 to 10 wt.-% of initiator,
c) 0 to 80 wt.-% of further monomer,
d) 0 to 80 wt.-% of filler,
e) 0 to 70 wt.-% of solvent.

9. Dental material according to claim 8 for use as an adhesive, which comprises 0 to 20 wt.-% of filler.

10. Dental material according to claim 9, which comprises
a) 0.1 to 50 wt.-% of polymerizable β-ketophosphonic acids of general formula I,
b) 0.01 to 10 wt.-% of initiator,
c) 0 to 60 wt.-% of non-acid mono- or multifunctional monomers and/or 0 to 60 wt.-% of acid monomers,
d) 0 to 20 wt.-% of filler,
e) 0 to 70 wt.-% of solvent.

11. Dental material according to claim 8 for use as a cement or filling material, which comprises 20 to 80 wt.-% of filler.

12. Dental material according to claim 1, for intraoral use as an adhesive, filling material or cement.

13. Method of using a dental material comprising extraorally producing dental restorations or repairing dental restorations with the dental material of claim 1.

14. Dental material according to claim 1, wherein
A=a linear $C_1$-$C_{10}$ radical which can be interrupted by 1 or 2 O atoms,
n=1,
m=1 or 2,
X=a $C_1$ or $C_2$ radical or is absent, and PG=vinyl, allyl, $CH_2=CR^2-CO-Y-$ or $R^3O-CO-C(=CH_2)-CH_2-Y-$, wherein Y is O or $NR^4$ or is absent, $R^2$ is H or $CH_3$ and $R^3$ and $R^4$ independently of each other are each H or $C_1$-$C_7$-alkyl.

15. Dental material according to claim 9, which comprises
a) 1 to 40 wt.-% of polymerizable β-ketophosphonic acids of general formula I,
b) 0.1 to 3.0 wt.-% of initiator,
c) 0 to 40 wt.-% of non-acid mono- or multifunctional monomers and/or 0 to 30 wt.-% of acid monomers,
d) 0 to 20 wt.-% of filler,
e) 0 to 60 wt.-% of solvent.

16. Dental material according to claim 9, which comprises
a) 2 to 30 wt.-% of polymerizable β-ketophosphonic acids of general formula I,
b) 0.01 to 10 wt.-% of initiator,
c) 5 to 40 wt.-% of non-acid mono- or multifunctional monomers and/or 0 to 60 wt.-% of acid monomers,
d) 0 to 20 wt.-% of filler,
e) 0 to 50 wt.-% of solvent.

\* \* \* \* \*